United States Patent [19]

Wu et al.

[11] Patent Number: 5,714,659
[45] Date of Patent: Feb. 3, 1998

[54] CATALYST COMPOSITION AND PROCESSES THEREFOR AND THEREWITH

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 705,917

[22] Filed: Aug. 29, 1996

[51] Int. Cl.$^6$ ............................................. C07C 4/11
[52] U.S. Cl. .................... 585/483; 585/486; 585/488; 585/489
[58] Field of Search ................................. 585/483, 486, 585/488, 489

[56] References Cited

U.S. PATENT DOCUMENTS

| | | | |
|---|---|---|---|
| 2,437,532 | 3/1948 | Huffman | 196/28 |
| 2,734,929 | 2/1956 | Doumani | 260/672 |
| 2,960,545 | 11/1960 | Seubold, Jr. | 260/672 |
| 3,213,153 | 10/1965 | Mills | 260/672 |
| 3,502,595 | 3/1970 | Johnson et al. | 252/437 |
| 3,857,901 | 12/1974 | Dowden et al. | 260/668 A |
| 3,923,639 | 12/1975 | Ciric | 208/111 |
| 3,954,670 | 5/1976 | Pine | 502/64 |
| 3,980,586 | 9/1976 | Mitchell | 252/455 R |
| 3,992,468 | 11/1976 | Cosyns et al. | 260/672 R |
| 4,005,048 | 1/1977 | Dowden et al. | 252/432 |
| 4,024,052 | 5/1977 | Antos | 208/139 |
| 4,080,284 | 3/1978 | Mitchell | 208/111 |
| 4,207,169 | 6/1980 | Courty et al. | 208/124 |
| 4,269,813 | 5/1981 | Klotz | 423/277 |
| 4,483,767 | 11/1984 | Antos et al. | 208/138 |
| 4,590,324 | 5/1986 | Satek | 585/444 |
| 4,677,240 | 6/1987 | Carlson et al. | 585/488 |
| 4,711,869 | 12/1987 | Cullo et al. | 502/251 |

*Primary Examiner*—Glenn Caldarola
*Assistant Examiner*—Thuan D. Dang
*Attorney, Agent, or Firm*—Lucas K. Shay

[57] ABSTRACT

A catalyst composition and a process for hydrodealkylating a $C_9+$ aromatic compound such as, for example, 1,2,4-trimethylbenzene to a $C_6$ to $C_8$ aromatic hydrocarbon such as a xylene are disclosed. The composition comprises an alumina, a metal oxide, and a acid site modifier selected from the group consisting of silicon oxides, boron oxides magnesium oxides, tin oxides, titanium oxides, zirconium oxides, molybdenum oxides, germanium oxides, indium oxides, lanthanum oxides, cesium oxides, and combinations of any two or more thereof. The process comprises contacting a fluid which comprises a $C_9+$ aromatic compound with the catalyst composition under a condition sufficient to effect the conversion of a $C_9+$ aromatic compound to a $C_6$ to $C_8$ aromatic hydrocarbon.

15 Claims, No Drawings

5,714,659

CATALYST COMPOSITION AND PROCESSES THEREFOR AND THEREWITH

FIELD OF THE INVENTION

This invention relates to a catalyst composition useful for converting a $C_9+$ aromatic compound to a $C_6$ to $C_8$ aromatic hydrocarbon and to a process for using the composition in a hydrodealkylation process.

BACKGROUND OF THE INVENTION

It is well known to those skilled in the art that aromatic hydrocarbons are a class of very important industrial chemicals which find a variety of uses in petrochemical industry. Recent efforts to convert gasoline to more valuable petrochemical products have therefore focused on the aromatization of gasoline to aromatic hydrocarbons by catalytic cracking in the presence of a catalyst. The aromatic hydrocarbons produced by the aromatization process include $C_6$ to $C_8$ hydrocarbons such as benzene, toluene and xylenes (hereinafter collectively referred to as BTX) which can be useful feedstocks for producing various organic compounds and polymers. However, heavier, less useful aromatic compounds are also produced during the aromatization process. It is, therefore, highly desirable to convert these compounds to the more useful BTX.

Though a chromium oxide-promoted alumina has been used as catalyst in dehydrogenation and hydrodealkylation processes, the conversion of a $C_9+$ aromatic compound and the selectivity to BTX are generally not as high as one skilled in the art would desire. It is also well known to one skilled in the art that alumina is an acidic metal oxide containing acid sites. One of the possible reasons for such low conversion and low selectivity is probably due to the acidity of an alumina-based catalyst.

Furthermore, a catalyst used in the hydrodealkylation of these heavier aromatic compounds is generally deactivated in a rather short period because of depositions of carbonaceous material such as, for example, coke on the surface of the catalyst.

Accordingly, there is an ever-increasing need to develop a catalyst and a process for converting these heavier and less useful aromatic compounds (mainly trimethyl- and tetramethylbenzenes) to the more valuable BTX hydrocarbons (hereinafter referred to as hydrodealkylation process) and, in the meantime, for suppressing the coke formation. Such development would also be a significant contribution to the art and to the economy.

SUMMARY OF THE INVENTION

An object of this invention is to provide a catalyst composition which can be used to convert a $C_9+$ aromatic compound to a $C_6$ to $C_8$ aromatic hydrocarbon. Also an object of this invention is to provide a process for producing the catalyst composition. Another object of this invention is to provide a process which can employ the catalyst composition to convert $C_9+$ aromatic compounds to $C_6$ to $C_8$ aromatic compounds. An advantage of the catalyst composition is that it decreases coke deposits thereon and exhibits high hydrodealkylation activity, satisfactory yield of xylenes and BTX, and good stability. Other objects and advantages will becomes more apparent as this invention is more fully disclosed hereinbelow.

According to a first embodiment of the present invention, a composition which can be used as a catalyst for converting a $C_9+$ aromatic compound to a $C_6$ to $C_8$ aromatic hydrocarbon is provided. The composition is a metal oxide-promoted alumina having incorporated therein an acid site modifier wherein the metal of the metal oxide is selected from the group consisting of chromium, cobalt, molybdenum, nickel, rhodium, palladium, platinum, tungsten, and combinations of any two or more thereof.

According to a second embodiment of the invention, a process for producing a composition which can be used as catalyst in a hydrodealkylation process is provided. The process comprises (1) contacting an alumina with an acid site modifier precursor selected from the group consisting of silicon-containing compounds, boron-containing compounds, magnesium-containing compounds, tin-containing compounds, titanium-containing compounds, zirconium-containing compounds, molybdenum-containing compounds, germanium-containing compounds, indium-containing compounds, lanthanum-containing compounds, cesium-containing compounds, and combinations of any two or more thereof under a condition sufficient to incorporate the acid site modifier into the metal alumina to form a first modified alumina; and (2) calcining the first modified alumina under a condition sufficient to convert the acid site modifier precursor to its oxide form to produce an acid site-modified alumina; (3) contacting the acid site-modified alumina with a metal compound whose metal is selected from the group consisting of chromium, cobalt, molybdenum, nickel, rhodium, palladium, platinum, tungsten, and combinations of any two or more thereof whereby a second modified alumina is formed; and (4) calcining the second modified alumina under a condition sufficient to effect the conversion of the metal compound to its corresponding metal oxide wherein the amount of the acid site modifier precursor is the amount that is sufficient to convert the metal compound to its oxide form.

According to a third embodiment of the present invention, a process which can be used for converting a $C_9+$ aromatic compound to a $C_6$ to $C_8$ aromatics compound is provided which comprises, consists essentially of, or consists of, contacting a fluid which comprises a $C_9+$ aromatic compound, optionally in the presence of an insert fluid such as a hydrogen-containing fluid, with a catalyst composition which is the same as disclosed above in the first embodiment of the invention under a condition effective to convert a $C_9+$ aromatic compound to an aromatic hydrocarbon containing 6 to 8 carbon atoms per molecule.

DETAILED DESCRIPTION OF THE INVENTION

According to the first embodiment of the invention, a composition which can be used as catalyst in a hydrodealkylation process for converting a $C_9+$ aromatic compound to a $C_6$ to $C_8$ aromatic hydrocarbon is provided. The composition comprises, consists essentially of, or consists of, a metal oxide-promoted alumina having incorporated therein, or impregnated thereon, a acid site modifier selected from the group consisting of silicon oxides, boron oxides, magnesium oxides, tin oxides, titanium oxides, zirconium oxides, molybdenum oxides, germanium oxides, indium oxides, lanthanum oxides, cesium oxides, and combinations of any two or more thereof wherein the acid site modifier is present in the composition in a selectivity-improving amount to improve the selectivity to BTX when the composition is used in a hydrodealkylation process. However, a phosphorus oxide is preferably excluded from the composition.

According to the first embodiment of the invention, the weight ratio of the acid site modifier to the metal oxide-promoted alumina can be any ratio so long as the ratio can suppress or reduce the formation or deposition of coke on a an alumina catalyst during the hydrodealkylation process for converting of a $C_9+$ aromatic compound to a $C_6$ to $C_8$ aromatic hydrocarbon. Generally, the ratio can be in the range of from about 0.0001:1 to about 1:1, preferably about 0.0005:1 to about 1:1, more preferably about 0.001:1 to about 0.8:1 and most preferably from 0.005:1 to 0.5:1 for an effective dehydroalkylation conversion and coke reduction or suppression. Alternatively, the acid site modifier can be present in the catalyst composition in the range of from about 0.01 to about 50, preferably about 0.05 to about 50, more preferably about 0.1 to about 45, and most preferably 0.5 to 33 grams per 100 grams of the catalyst composition.

Any metal oxide-promoted alumina which is known to one skilled in the art to be capable of catalyzing a hydrodealkylation of a $C_9+$ aromatic compound to a $C_6$ to $C_8$ aromatic hydrocarbon can be employed in the present invention. The alumina can be α-alumina, β-alumina, γ-alumina, δ-alumina, η-alumina, and combinations of any two or more thereof. The presently preferred alumina is a γ-alumina having a surface area in the range of from about 40 to about 300 $m^2/g$, a total pore volume in the range of from about 0.1 to about 1.

Any metal oxide that, when incorporated into an alumina, is capable of promoting the hydrodealkylation of a $C_9+$ aromatic compound to a $C_6$ to $C_8$ aromatic hydrocarbon be employed in the invention. Presently, it is preferred that the metal oxide is selected from the group consisting of chromium oxides, cobalt oxides, molybdenum oxides, nickel oxide, rhodium oxides, palladium oxides, platinum oxides, tungsten oxides, and combinations of any two or more thereof wherein the oxidation state of the metal can be any available oxidation state. For example, in the case of a chromium oxide, the oxidation state of chromium can be either 3 or 6. The presently preferred metal oxide-promoted alumina is a $Cr/Al_2O_3$ wherein the $Cr/Al_2O_3$ denotes an alumina promoted with both a chromium oxide. The presently more preferred metal oxide is a chromium(III) oxide. These metal oxide-promoted aluminas are commercially available. However, it is preferred they be produced by the process disclosed in the second embodiment of the invention. The weight percent (%) of a metal oxide to the catalyst composition can be any weight % so long as such weight % can be effective on a hydrodealkylation process. The weight % can be in the range of from about 0.1% to about 60%, preferably about 0.5 to about 50%, and most preferably 1 to 40%. If a combination of metal oxides is employed, the molar ratio of the second metal oxide, or the third metal oxide, or the fourth metal oxide to the first metal oxide can be in the range of about 0.01:1 to about 100:1.

According to the present invention, any acid site modifier that, as compared to use of a metal oxide-promoted alumina only, can effect the reduction of coke deposition on the metal oxide-promoted alumina during the conversion of a $C_9+$ aromatic compound to a $C_6$ to $C_8$ aromatic hydrocarbon can be employed. Presently it is preferred that the acid site modifier is selected from the group consisting of silicon oxides, phosphorus oxides, boron oxides, magnesium oxides, tin oxides, titanium oxides, zirconium oxides, molybdenum oxides, germanium oxides, indium oxides, lanthanum oxides, cesium oxides, and combinations of any two or more thereof.

Any methods known to one skilled in the art for incorporating a compound or a portion thereof into an alumina such as, for example, impregnation or extrusion can be employed for producing the composition of the present invention. However, it is presently preferred the composition be produced by the process disclosed in the second embodiment of the invention.

As disclosed above, the alumina can be α-alumina, β-alumina, γ-alumina, and combinations of any two or more thereof. The presently preferred alumina is γ-alumina having a surface area in the range of from about 40 to about 300 $m^2/g$, a total pore volume in the range of from about 0.1 to about 1. These aluminas are commercially available.

An alumina is generally first treated with a acid site modifier precursor. According to the second embodiment of the present invention, any acid site modifier precursor which can be converted to a acid site modifier, as disclosed in the first embodiment of the invention, that, as compared to use of a metal oxide-promoted alumina only, can effect the improvement of selectivity to BTX or xylene reduction of coke in a hydrodealkylation process can be employed. Presently it is preferred that a acid site modifier precursor be selected from the group consisting of boron-containing compounds, magnesium-containing compounds, tin-containing compounds, titanium-containing compounds, zirconium-containing compounds, molybdenum-containing compounds, germanium-containing compounds, indium-containing compounds, lanthanum-containing compounds, cesium-containing compounds, and combinations of any two or more thereof.

Generally any silicon-containing compounds which can be converted to a silicon oxide that are effective to enhance hydrodealkylation of a $C_9+$ aromatic compound when used with a metal oxide-promoted alumina can be used in the present invention. Examples of suitable silicon-containing compounds can have a formula of $(R)(R)(R)Si-(O_mSi(R)(R))_n R$ wherein each R can be the same or different and is independently selected from the group consisting of alkyl radicals, alkenyl radicals, aryl radicals, alkaryl radicals, aralkyl radicals, and combinations of any two or more thereof; m is 0 or 1; and n is 1 to about 10 wherein each radical can contain 1 to about 15, preferably 1 to about 10 carbon atoms per radical. Specific examples of such polymers include, but are not limited to, silicon-containing polymers such as poly(phenylmethylsiloxane), poly(phenylethylsiloxane), poly(phenylpropylsiloxane), hexamethyldisiloxane, decamethyltetrasiloxane, diphenyltetramethyldisiloxane, and combinations of any two or more thereof. Other silicon-containing compounds include organosilicates such as, for example, tetraethyl orthosilicate tetrabutyl orthosilicate, tetrapropyl orthosilicate, or combination of any two or more thereof. A number of well known silylating agents such as trimethylchlorosilane, chloromethyldimethylchlorosilane, N-trimethylsilylimidazole, N,O-bis(trimethylsilyl)acetimide, N-methyl-N-trimethylsilyltrifluoroacetamie, t-butyldimethylsilylimidazole, N-trimethylsilylacetamide, methyltrimethoxysilane, vinyltriethoxysilane, ethyltrimethoxysilane, propyltrimethoxysilane, (3,3,3-trifluoropropyl)trimethoxysilane, [3-(2-aminoethyl)aminopropyl]trimethoxysilane, cyanoethyltrimethoxysilane, aminopropyltriethoxysilane, phenyltrimethoxysilen, (3-chloropropyl)trimethoxysilane, (3-mercaptopropyl)trimethoxysilane, (3-glycidoxypropyl)trimethoxysilane, vinyltris(β-methoxyethoxy)silane, (γ-methacryloxypropyl)trimethoxysilane, vinylbenzyl cationic silane, (4-aminopropyl)triethoxysilane, [γ-(β-aminoethylamino)propyl]trimethoxysilane, (γ-glycidoxypropyl)trimethoxysilane, [β-(3,4-epoxycyclohexyl)ethyl]trimethoxysilane, (β-mercaptoethyl)trimethoxysilane, (γ-chloropropyl)trimethoxysilane, and combinations of any two or more thereof can also be employed. The presently preferred silicon-containing compounds are tetraethyl orthosilicate and poly(phenylmethyl) siloxane.

According to the present invention, any boron-containing compound which, upon being incorporated into a metal oxide-promoted alumina can be converted into a boron oxide upon calcining can be used in the present invention. A boron compound having a formula of $BR_{3-z}W_z$, $(R'BO)_z$, $BW_z$, $B(OR)_3$, or combinations of any two or more thereof can be used in the present invention in which R is the same as above, R' can be R, RO, RS, $R_2N$, $R_2P$, $R_3Si$, or combinations of any two or more thereof, W can be a halogen, $NO_3$, $NO_2$, $SO_4$, $PO_4$, or combinations of any two or more thereof, and z is an integer of 1 to 3. Examples of suitable boron-containing compounds include, but are not limited to boric acid, borane-ammonium complex, boron trichloride, boron phosphate, boron nitride, triethyl borane, trimethyl borane, tripropyl borane, trimethyl borate, triethyl borate, tripropyl borate, trimethyl boroxine, triethyl boroxine, tripropyl boroxine, and combinations of any two or more thereof.

Examples of suitable magnesium-containing compounds include, but are not limited to, magnesium formate, magnesium acetate, magnesium bromide, magnesium bromide diethyl etherate, magnesium chloride, magnesium fluoride, magnesium nitrate, magnesium sulfate, dibutyl magnesium, magnesium methoxide, and combinations of any two or more thereof.

Similarly, examples of suitable tin-containing compound include, but are not limited to, stannous acetate, stannic acetate, stannous bromide, stannic bromide, stannous chloride, stannic chloride, stannous oxalate, stannous sulfate, stannic sulfate, stannous sulfide, and combinations of any two or more thereof.

Some of the titanium-containing compounds suitable for use in the invention include, but are not limited to, titanium tetrahydrocarbyloxide having the formula of $Ti(OR)_4$, titanium tetraamides, titanium tetramercaptides, organotitanium compounds having the formula of $TiX_p(OR)_{4-p}$, organic or inorganic titanates, titanate chelates, and combinations of any two or more thereof wherein p is an integer of 1 to 4. Examples of suitable titanium-containing compounds include, but are not limited to, titanium zinc titanate, lanthanum titanate, titanium tetramides, titanium tetramercaptides, titanium tetrabutoxide $(Ti(OC_4H_9)_4)$, titanium tetramethoxides $(Ti(OCH_4)_4)$, titanium tetraethoxide $(Ti(OC_2H_5)_4)$, titanium tetrapropoxide $Ti(OC_3H_7)_4$, titanium tetrachloride, titanium trichloride, titanium bromides, triethanolamine titanate chelate, lactic acid titanate chelate, and combinations of any two or more thereof.

Similarly, examples of suitable zirconium-containing compounds include, but are not limited to, zirconium acetate, zirconium formate, zirconium chloride, zirconium bromide, zirconium butoxide, zirconium tert-butoxide, zirconium chloride, zirconium citrate, zirconium ethoxide, zirconium methoxide, zirconium propoxide, and combinations of any two or more thereof.

Suitable molybdenum-containing compounds include, but are not limited to, molybdenum(III) chloride, molybdenum (II) acetate, molybdenum(IV) chloride, molybdenum(V) chloride, molybdenum(VI) fluoride, molybdenum(VI) oxychloride, molybdenum(IV) sulfide, ammonium heptamolybdate(VI) and combinations of two or more thereof.

Examples of suitable germanium-containing compounds include, but are not limited to, germanium chloride, germanium bromide, germanium ethoxide, germanium fluoride, germanium iodide, germanium methoxide, and combinations of any two or more thereof. Examples of suitable indium-containing compounds include, but are not limited to indium acetate, indium bromide, indium chloride, indium fluoride, indium iodide, indium nitrate, indium phosphide, indium selenide, indium sulfate, and combinations of any two or more thereof.

Examples of suitable lanthanum-containing compounds include, but are not limited to, lanthanum acetate, lanthanum carbonate, lanthanum octanoate, lanthanum fluoride, lanthanum chloride, lanthanum bromide, lanthanum iodide, lanthanum nitrate, lanthanum perchlorate, lanthanum sulfate, lanthanum titanate, and combinations of any two or more thereof.

Generally, in the first step of the process of the second embodiment of the invention, an alumina can be combined with such acid site modifier precursor in any suitable weight ratios which would result in the weight ratios of a acid site modifier to a metal oxide-promoted alumina disclosed in the first embodiment of the invention. Presently it is preferred that such combination be carried out in a suitable liquid, preferably an aqueous medium, to form an incipient wetness alumina-precursor mixture.

Upon the alumina and the precursor are well mixed, in the second step of the process, the alumina-precursor mixture is subjected to calcination under a condition that can include a temperature in the range of from about 300° C. to about 1000° C., preferably about 350° C. to about 750° C., and most preferably 400° C. to 650° C. under a pressure in the range of from about 1 to about 10, preferably about 1 atmospheres for a period in the range of from about 1 to about 30, preferably about 1 to about 20, and most preferably 1 to 15 hours.

Upon completion of incorporating the acid site modifier into the alumina by calcination, an acid site-modified alumina is formed. In the third step of the process, the acid site-modified aluminum is then contacted, generally mixed, with a metal compound which can be converted, in the fourth step of the process, to a metal oxide shown in the first embodiment of the invention. In this third step, a second modified alumina is produced. The contacting can be carried out by the same procedure as disclosed in the first step of the second embodiment of the invention. The metal of a suitable metal compound is selected from the group consisting of chromium, cobalt, molybdenum, nickel, rhodium, palladium, platinum, tungsten, and combinations of any two or more thereof.

Examples of suitable metal compounds include, but are not limited to, chromium(II) acetate, chromium(III) acetate, chromium(III) acetylacetonate, chromium(II) chloride, chromium(III) chloride, chromium(II) fluoride, chromium (III) fluoride, chromium hexacarbonyl, chromium(III) nitrate, chromium nitride, chromium(III) 2,4-pentanedionate, chromium(III) perchlorate, chromium(III) potassium sulfate, chromium(III) sulfate, chromium(III) telluride, cobalt(II) acetate cobalt(II) acetylacetonate, cobalt (III) acetylacetonate, cobalt(II) benzoylacetonate, cobalt(II) bromide, cobalt(II) carbonate, cobalt(II) chloride, cobalt(II) 2-ethylhexanoate, cobalt(II) fluoride cobalt(III) fluoride, cobalt(II) iodide, cobalt(II) iodide, cobalt(II) 2,3-naphthalocyanine, cobalt(II) nitrate, cobalt(II) oxalate, cobalt(II) perchlorate, cobalt(II) phthalocyanine, cobalt(II) sulfate, cobalt(II) thiocyanate, cobalt(II) tungstate, molybdenum(II) acetate, molybdenum(III) bromide, molybdenum(II) chloride, molybdenum(IV) chloride, molybdenum(V) chloride, molybdenum hexacarbonyl, molybdenum(IV) sulfide, molybdenum(VI) tetrachloride oxide, nickel(II) acetate, nickel(II) acetylacetonate, nickel (II) bromide, nickel(II) carbonate, nickel(II) chloride, nickel (II) nitrate, nickel(II) perchlorate, nickel phosphide, nickel (II) sulfate, nickel sulfide, nickel(II) titanate, palladium(II) acetate, palladium(II) acetylacetonate, palladium(II) bromide, palladium(II) iodide, palladium(II) nitrate, palladium(II) sulfate, palladium(II) sulfide, rhodium(II) acetate, rhodium(III) acetylacetonate, rhodium(III) bromide, rhodium(III) chloride, rhodium(III) nitrate, rhodium(II) octanoate, rhodium(III) phosphate, rhodium(III) sulfate, tungsten(V) bromide, tungsten(IV) chloride, tungsten(VI) chloride, tungsten hexacarbonyl, tungsten(VI) oxychloride, tungsten(IV) sulfide, tungstic acid, and combinations of any two or more thereof. The presently preferred metal compounds include, but are not limited to, chromium(II) acetate, chromium(III) acetate, chromium(III) acetylacetonate, chromium(II) chloride, chromium(III) chloride, chromium (II) fluoride, chromium(III) fluoride, chromium hexacarbonyl, chromium(III) nitrate, chromium nitride, chromium(III) 2,4-pentanedionate, chromium(III) perchlorate, chromium(III) potassium sulfate, chromium (III) sulfate, chromium(III) telluride, and combinations of any two or more thereof. The presently most preferred metal compound is chromium(III) nitrate for it is readily available and effective.

In the next step, the second modified alumina is calcined to produce the composition of the invention. The calcination conditions can be the same as those disclosed above in the second step of the process.

The composition of the invention then can be, if desired, pretreated with a reducing agent before being used in a hydrodealkylation process. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 650° C. for 1 to 5 hours.

According to the third embodiment of the present invention, a process useful for converting a $C_9+$ aromatic compound to a $C_6$ to $C_8$ aromatic hydrocarbon comprises, consists essentially of, or consists of contacting a fluid stream comprising a $C_9+$ aromatic compound and, optionally, in the presence of an inert fluid such as, for example, hydrogen-containing fluid, with a catalyst composition under a condition sufficient to effect the conversion of a $C_9+$ aromatic compound to a $C_6$ to $C_8$ aromatic hydrocarbon. The term "inert fluid" refers to a fluid that does not substantially react with a $C_9+$ aromatic compound. The inert fluid can be hydrogen, nitrogen, helium, argon, carbon dioxide, neon, steam, and combinations of any two or more thereof. The presently preferred inert fluid is a hydrogen-containing fluid. The inert fluid can also be fed separately into contact with a $C_9+$ aromatic compound and a catalyst. The catalyst composition is the same as that disclosed in the first embodiment of the invention.

The term "fluid" is used herein to denote gas, liquid, vapor, or combinations of two or more thereof. The term "$C_9+$ aromatic compound" is referred to, unless otherwise indicated, as a substituted aromatic compound containing at least 9 carbon atoms per molecule. Preferably the substituted aromatic compound has the formula of $R'_q Ar$ wherein each R' is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, q is a whole number from 1 to 5, and Ar is a phenyl group. More preferably R' is an alkyl radical having 1 to about 10 carbon atoms and the aromatic compound has 9 to about 16 carbon atoms per molecule. Most preferably the aromatic compound contains 9 to 12 carbon atoms per molecule.

Any fluid which contains a $C_9+$ aromatic compound as disclosed above can be used as the feed for the process of this invention. The origin of this fluid feed is not critical. However, a preferred fluid feed is a $C_9+$ aromatic compound derived from the heavies fraction of a product from a paraffin, in particular gasoline, aromatization reaction. Generally, this heavies fraction contains primarily trimethylbenzenes such as 1,2,3-trimethylbenzene, 1,2,4-trimethylbenzene, and 1,3,5-trimethylbenzene and tetramethylbenzenes such as 1,2,3,4-tetramethylbenzene, 1,2,3,5-tetramethylbenzene and 1,2,4,5-tetramethylbenzene. Additionally, n-propylbenzene, 3-ethyltoluene, 4-ethyltoluene, 3-n-propyltoluene, 4-n-propyltoluene, and 1,3-diethylbenzene can also be present in the fluid. Benzene, toluene, ethylbenzene and xylenes are generally substantially absent from the fluid, i.e., the amount of each of these aromatic hydrocarbons is less than about 0.1 weight %. Thus, there is no significant alkylation of these lower aromatic hydrocarbons by the $C_9+$ aromatic compound, i.e., no significant transalkylation occurs as a side-reaction in the process of this invention. To demonstrate the process of the invention, a trimethyl benzene such as 1,2,4-trimethylbenzene was used.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of any two or more thereof, or any other fluid which does not significantly affect the process or the catalyst composition used therein.

The contacting of a fluid containing a $C_9+$ aromatic compound, in the presence or absence of a hydrogen-containing fluid, with a catalyst composition can be carried out in any technically suitable manner, in batch, semicontinuous, or continuous process under a condition effective to convert a $C_9+$ aromatic compound to a $C_6$ to $C_8$ aromatic hydrocarbon. Generally, a fluid containing a $C_9+$ aromatic compound, preferably being in the vaporized state, and a hydrogen-containing fluid are introduced into a fixed catalyst bed, or a moving catalyst bed, or a fluidized catalyst bed, or combinations of any two or more thereof by any means known to one skilled in the art such as, for example, pressure, meter pump, and other similar means. The condition can include an hourly space velocity (HSV) of the $C_9+$ aromatic compound fluid stream in the range of about 0.01 to about 100, preferably about 0.05 to about 50, and most preferably 0.1 to 30 g feed/g catalyst/hour. The hydrogen-containing fluid hourly space velocity generally is in the range of about 1 to about 10,000, preferably about 5 to about 7,000, and most preferably 10 to 5,000 $ft^3$ $H_2/ft^3$ catalyst/hour. The preferred molar ratio of $H_2$ to the $C_9+$ aromatic compound can be in the range of from about 0.01:1 to about 20:1, preferably about 0.1:1 to about 10:1, and most preferably 0.5:1 to 5:1. Generally, the pressure can be in the range of from about 30 to about 1000 psig., preferably about 50 to about 750 psig, and most preferably 200 to 600 psig, and the temperature is about 250° to about 1,000° C., preferably about 350° to about 800° C., and most preferably 400° C. to 650° C.

The process effluent generally contains a heavies fraction of unconverted $C_9+$ aromatics and other heavy ($C_9+$) aromatic compounds which may have been formed by side-reactions (such as isomerization); a lights fraction of alkanes, mainly methane, ethane, propane, n-butane, isobutane, and minor amounts (about 0.1 to about 5 weight %) of $C_5$ and $C_6$ alkanes such as, for example, isopentane and n-pentane; and a BTX aromatic hydrocarbons fraction (benzene, toluene, ortho-xylene, meta-xylene and para-xylene). Generally, the effluent can be separated into these principal fractions by fractionation distillation which is well known to one skilled in the art. The heavies fraction can be recycled to a hydrodealkylation reactor described above, the lights fraction can be used as fuel gas or as a feed for other reactions such as, for example, in a thermal cracking process to produce ethylene and propylene, and the BTX fraction can be further separated into individual $C_6$ to $C_8$ aromatic hydrocarbon fractions. Alternatively, the BTX fraction can undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes) involving transalkylation benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the most valuable $C_6$ to $C_8$ aromatic product (generally xylenes) have become unsatisfactory, the catalyst composition can be reactivated by any means known to one skilled in the art such as, for example, calcining in air to burn off deposited coke and other carbonaceous materials, such as oligomers or polymers, preferably at a temperature of about 400° to about 650° C., followed by a treatment with a reducing agent such as, for example, with hydrogen gas at a temperature of about 400° to about 600° C. The optimal time periods of the calcining and treatment with a reducing agent depend generally on the types and amounts of deactivating deposits on the catalyst composition and on the calcination and reduction temperatures. These optimal time periods can easily be determined by those possessing ordinary skills in the art and are omitted herein for the interest of brevity.

The following examples are presented to further illustrate this invention and are not to be construed as unduly limiting the scope of the present invention.

EXAMPLE I

This example illustrates the preparation of catalyst compositions of the invention and the use of the composition in a hydrodealkylation process.

A γ-alumina obtained as ¹⁄₁₆ inch extrudates from Criterion Catalyst Company L.P., Michigan City, Ind. was used. Thereafter, 100 g of the alumina was calcined at 525° C. for 3 hours to produce a calcined alumina (control catalyst A).

A portion (14.0 g) of the calcined alumina (catalyst A) was well mixed with 10.76 g of 50 weight % $Cr(NO_3)_3.9H_2O$ followed by calcining at 525° C. in air to produce 15.23 g of chromium oxide-promoted alumina (control catalyst B) containing 4.59 weight % of chromium oxide.

Separately, a portion of the calcined alumina (14.0 g) (catalyst A) was well mixed with 6.0 g of a 50 weight % tripropyl borate, $B(OCH_2CH_2CH_3)_3$ (obtained from Aldrich Chemical Co., Milwaukee, Wis., in cyclohexane followed by calcining the resulting mixture in air in a furnace at 538° C. for 6 hours to produce 14.49 g of a boron oxide-incorporated alumina containing 3.38 weight % boron oxide by calculation. A portion (4.83 g) of this boron oxide-incorporated alumina was then well mixed with 3.13 g of 50 weight % $Cr(NO_3)_3.9H_2O$ followed by calcining at 538° C. in air for 6 hours to produce 5.15 g of a boron oxide-incorporated, chromium oxide-promoted alumina (Cr/$Al_2O_3$) containing 3.949 weight % chromium oxide by calculation (invention catalyst C).

Further separately, a portion (14.0 g) of the calcined alumina (catalyst A) was well mixed with 8.22 of a 30 weight % lanthanum nitrate ($La(NO_3)_3.6H_2O$) solution (obtained from Aldrich Chemical Co., Milwaukee, Wis.) to form a mixture. The mixture was calcined at 525° C. in a furnace to produce 14.53 g of lanthanum oxide-incorporated alumina containing 5.444 weight % (by calculation) of lanthanum oxide). A portion (7.27 g) of this lanthanum oxide-incorporated alumina was further well blended with 8.60 g of 50 weight % $Cr(NO_3)_3.9H_2O$ solution followed by calcination at 525° C. for 6 hours to produce 15.49 g of a lanthanum oxide-incorporated, chromium oxide-promoted alumina (Cr/$Al_2O_3$) containing 3.607 weight % of chromium oxide by calculation (invention catalyst D).

In a further separate run, 14.0 g of catalyst A was well mixed with 6.72 g of a solution of 50 weight % diisopropyl-bis(triethanolamine) orthotitanate or triethanolamine titanate chelate (obtained from DuPont de Nemours and Co., Wilmington, Del. under a trademark of TYZOR® TE in water to form a mixture. The mixture was subsequently calcined at 538° C. in air in a furnace for 6 hours to produce 14.35 g of a titanium oxide-incorporated alumina containing 2.34 weight % of titanium oxide by calculation. A portion (4.78 g) of this titanium oxide-incorporated alumina was further well mixed with 3.69 g of 50 weight % chromium nitrate ($Cr(NO_3)_3.9H_2O$) solution followed by calcining the resulting mixture at 538° C. for 6 hours in air to produce 5.10 g of a titanium oxide-incorporated, chromium oxide-promoted alumina containing 4.153 weight % of chromium oxide by calculation (invention catalyst E).

These chromium-promoted aluminas were then employed, according to the third embodiment of the invention, in a hydrodealkylation process for convering 1,2,4-trimethylbenzene to BTX. The 1,2,4-trimethylbenzene was obtained from Phillips Petroleum Company, Bartlesville, Okla., and was employed as feedstock. The hydrodealkylation process was carried out as follows.

A stainless-steel reactor tube (inner diameter 0.75 inch; length 20 inches) was filled with a 20 ml bottom layer of Alundum® alumina (inert, low surface area alumina), one of the catalysts (in ¹⁄₁₆ inch extrudates) in the center position 5 ml, and a 20 ml top layer of Alundum® alumina. The catalysts were pretreated with hydrogen (260 ml/minute) at 575° C. (starting at 25° C. then ramping at 10° C./min) for one hour. The 1,2,4-trimethylbenzene feed was then introduced into the reactor at a rate of 20 milliliters/hour (WHSV=5.1), together with hydrogen gas at a rate of 260 ml of $H_2$/hours (molar ratio of $H_2$ to 1,2,4-trimethylbenzene was 5). The reaction temperature was 575° C. to 579° C. as shown in Table I, and the reaction pressure was 500 psig. The reactor effluent was cooled and analyzed with an on-line gas chromatograph at intervals of about 1 hour. The results are shown in Table I.

TABLE I

| Catalyst | Catalyst Weight (g) | Reaction Temp (°C.) | Reaction Time (hr) | Reactor Effluent (wt %)[a] | | | | Conversion %[b] | Coke |
|---|---|---|---|---|---|---|---|---|---|
| | | | | Lights | BTX | Xyl | $C_9+$ | | |
| Control A | 2.92 | 575 | 6.67 | 0.4 | 6.2 | 5.3 | 92.5 | 7.5 | ND |
| Control B | 3.49 | 575 | 6.80 | 0.1 | 30.2 | 27.2 | 69.6 | 30.4 | 12.4 |
| Invention C | 3.71 | 575 | 6.20 | 2.0 | 37.5 | 32.7 | 60.5 | 39.5 | 4.0 |
| Invention D | 3.84 | 579 | 6.65 | 1.7 | 40.5 | 34.9 | 57.8 | 42.2 | ? |
| Invention E | 3.64 | 575 | 6.93 | 1.8 | 36.2 | 31.3 | 62.0 | 38.0 | ? |

[a] The values presented, except conversion, are weight percent. Xyl denotes the total weight % of all xylenes. The lights fraction included hydrocarbons shown in the text. The coke was determined at the end of a 7 hour run by removing the catalyst from the reactor and determined with a thermal gravimetric analyzer (TGA), manufactured by TA Instruments, New Castle, Delaware. ND denotes not determined.
[b] The % conversion was calculated as 100% − weight % $C_9+$.

The results shown in Table I indicate that the control catalyst B was heavily covered with coke (12.4%). The invention catalyst C which was incorporated with lanthanum oxide significantly reduced the coke deposition to 4.0 weight %. Furthermore, the invention catalysts C and D exhibited significantly higher conversion of 1,2,4-trimethylbenzene and higher yields of both BTX and xylenes than the control catalysts A and B did.

EXAMPLE II

This example illustrates another acid site-modified, chromium oxide-promoted alumina composition of the invention and processes therewith.

The catalyst composition was prepared by the same procedure as that disclosed in Example I except that 8.50 g of 50 weight % phosphoric acid ($H_3PO_4$) was used in place of a PPMS to treat catalyst A to produce a phosphorus oxide-incorporated $Cr/Al_2O_3$ catalyst containing 17 weight % phosphorus oxide and 2.852 weight % chromium oxide.

The thus-prepared catalyst (4.14 g) was used in a hydrodealkylation process for converting 1,2,4-trimethylbenzene to BTX using the procedure disclosed in Example I at 575° C. The results showed that, 6.30 hours after the process started, the reactor effluent contained 0.2 weight % lights, 25.2 weight % BTX, and 22.9 weight % of xylenes. It appears that incorporation of phosphorus oxide in fact decreased the yield of BTX.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed:

1. A process comprising contacting a fluid which comprises a $C_9+$ aromatic compound, in the presence of an inert fluid, with a catalyst composition under a condition sufficient to effect the conversion of a $C_9+$ aromatic compound to a $C_6$ to $C_8$ aromatic hydrocarbon wherein said catalyst composition comprises a metal oxide-promoted alumina having impregnated thereon boron oxide;

the metal of said metal oxide is selected from the group consisting of cobalt, molybdenum, nickel, rhodium, palladium, platinum, chromium, tungsten, and combinations of any two or more thereof;

the weight ratio of said boron oxide to said metal oxide-promoted aluminum is in the range of from about 0.0001:1 to about 1.1; and the weight percent of said metal oxide in said catalyst composition is in the range of from about 0.1 to about 60%.

2. A process according to claim 1 wherein said $C_9+$ aromatic compound comprises an aromatic hydrocarbon selected from the group consisting of 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, 1,3-diethylbenzene, and combinations of any two or more thereof.

3. A process according to claim 1 wherein said $C_9+$ aromatic compound is 1,2,4-trimethylbenzene.

4. A process according to claim 1 wherein the weight ratio of said boron oxide to said metal oxide-promoted alumina is in the range of from 0.005:1 to 0.5:1.

5. A process according to claim 1 wherein said metal oxide is a chromium oxide.

6. A process according to claim 1 wherein the weight % of said metal oxide in said catalyst composition is in the range of from 1 to 40%.

7. A process according to claim 6 wherein said metal oxide is a chromium oxide.

8. A process according to claim 1 wherein said catalyst composition comprises boron oxide, chromium oxide, and γ-alumina.

9. A process according to claim 8 wherein said aromatic compound is 1,2,4-trimethylbenzene.

10. A process according to claim 8 wherein said condition comprises a liquid hourly space velocity of said fluid in the range of about 0.1 to about 30 g feed/g catalyst/hour, a gas hourly space velocity of said hydrogen-containing fluid in the range of about 10 $ft^3$ gas/$ft^3$ catalyst/hour to about 5,000 $ft^3/ft^3$ catalyst/hour, a molar ratio of hydrogen to said $C_9+$ aromatic compound in the range of about 0.5:1 to about 5:1, a pressure in the range of about 50 psig to about 750 psig, and a temperature in the range of about 250° C. to about 1000° C.

11. A hydrodealkylation process comprising contacting, in the presence of a hydrogen-containing fluid, a fluid comprising a $C_9+$ aromatic compound with a catalyst composition under a condition sufficient to effect the conversion of said $C_9+$ aromatic compound to a $C_6$ to $C_8$ aromatic hydrocarbon wherein said catalyst composition is prepared by the steps comprising: (1) contacting an alumina with a boron-containing compound under a condition sufficient to impregnate said boron-containing compound onto said alumina to form a first modified alumina; (2) calcining said first modified alumina under a condition sufficient to convert boron-containing compound to its oxide form to produce an acid site-modified alumina; (3) contacting said acid site-modified alumina with a metal compound whose metal is selected from the group consisting of chromium, cobalt, molybdenum, nickel, rhodium, palladium, platinum, tungsten, and combinations of any two or more thereof to form a second modified alumina; and (4) calcining said second modified alumina under a condition sufficient to effect the conversion of said metal compound to its corresponding metal oxide.

12. A process according to claim 11 wherein said boron-containing compound is selected from the group consisting of $BR_{3-z}W_z$, $(R'BO)_z$, $BW_z$, $B(OR)_3$, or combinations of any two or more thereof wherein each R has one to about 10 carbon atoms and is independently selected from the group consisting of an alkyl radical, an alkenyl radical, an aryl radical, an aralkyl radical, an alkaryl radical, and combinations of any two or more thereof; each R' is independently selected from the group consisting of R, RO, RS, $R_2N$, $R_2P$, $R_3Si$, and combinations of any two or more thereof; each W is independently selected from the group consisting of a halogen, $NO_3$, $NO_2$, $SO_4$, $PO_4$, and combinations of any two or more thereof; and z is an integer of 1 to 3.

13. A process according to claim 11 wherein said boron-containing compound is selected from the group consisting of boric acid, borane-ammonium complex, boron trichloride, boron phosphate, boron nitride, triethyl borane, trimethyl borane, tripropyl borane, trimethyl borate, triethyl borate, tripropyl borate, trimethyl boroxine, triethyl boroxine, tripropyl boroxine, and combinations of any two or more thereof.

14. A process according to claim 11 wherein said boron-containing compound is tripropyl borate.

15. A process according to claim 14 wherein the metal of said metal compound is chromium.

* * * * *

UNITED STATES PATENT AND TRADEMARK OFFICE
CERTIFICATE OF CORRECTION

PATENT NO.   : 5,714,659

DATED        : February 3, 1998

INVENTOR(S)  : An-hsiang Wu and Charles A. Drake

It is certified that error appears in the above-identified patent and that said Letters Patent is hereby corrected as shown below:

Column 13, claim 12, line 12, the ":" before "containing should be deleted.

Column 13, claim 12, line 19, "R2N" should read "$R_2N$".

Signed and Sealed this

Twenty-eighth Day of April, 1998

Attest:

BRUCE LEHMAN

*Attesting Officer*    *Commissioner of Patents and Trademarks*